(12) United States Patent
Högele et al.

(10) Patent No.: US 10,842,374 B2
(45) Date of Patent: Nov. 24, 2020

(54) OPERATING MICROSCOPE

(71) Applicant: Carl Zeiss Meditec AG, Jena (DE)

(72) Inventors: Artur Högele, Oberkochen (DE); Christian Beder, Aalen (DE); Joachim Steffen, Westhausen (DE)

(73) Assignee: CARL ZEISS MEDITEC AG, Jena (DE)

( * ) Notice: Subject to any disclaimer, the term of this patent is extended or adjusted under 35 U.S.C. 154(b) by 65 days.

(21) Appl. No.: 15/800,746

(22) Filed: Nov. 1, 2017

(65) Prior Publication Data

US 2018/0125360 A1 May 10, 2018

(30) Foreign Application Priority Data

Nov. 4, 2016 (DE) .......... 10 2016 013 080
Mar. 15, 2017 (DE) .......... 10 2017 105 580

(51) Int. Cl.
*A61B 3/13* (2006.01)
*G02B 21/00* (2006.01)
(Continued)

(52) U.S. Cl.
CPC ............. *A61B 3/13* (2013.01); *A61B 90/20* (2016.02); *A61F 9/007* (2013.01); *G02B 15/04* (2013.01);
(Continued)

(58) Field of Classification Search
CPC .. A61B 3/00; A61B 3/13; A61B 90/20; A61B 3/12; A61B 3/14; A61B 3/102;
(Continued)

(56) References Cited

U.S. PATENT DOCUMENTS 4,769,530 A * 9/1988 Miyahara ............. G02B 21/247
250/201.4
4,786,161 A * 11/1988 Muller ................... A61B 3/156
351/205

(Continued)

FOREIGN PATENT DOCUMENTS

DE 35 39 009 5/1987
DE 602 20 630 2/2008
(Continued)

OTHER PUBLICATIONS

German Office Action for 10 2017 105 580.0 dated Jun. 2, 2017.

*Primary Examiner* — James R Sheleheda
(74) *Attorney, Agent, or Firm* — Nixon Peabody LLP; Jeffrey L. Costellia

(57) ABSTRACT

An operating microscope (2, 48) for observing an eye (77) is provided. The operating microscope (2, 48) comprises a main objective (5) and a fundus imaging system (71) that is positionable in the beam path (7) between the eye (77) and the main objective (5), said fundus imaging system having an ophthalmoscopy magnifier (73). The main objective (5) of the operating microscope (2, 48) has a focal length in the range between 90 mm and 160 mm. The fundus imaging system (71) also can comprise an optics group (81), the dispersion properties of which are matched to the dispersion properties of the ophthalmoscopy magnifier (73) in such a way that the optics group (81) compensates a chromatic aberration of the ophthalmoscopy magnifier (73).

12 Claims, 6 Drawing Sheets

(51) Int. Cl.

| | |
|---|---|
| *G02B 21/22* | (2006.01) |
| *G02B 15/14* | (2006.01) |
| *A61B 90/20* | (2016.01) |
| *G02B 15/04* | (2006.01) |
| *G02B 27/00* | (2006.01) |
| *A61B 3/14* | (2006.01) |
| *A61B 3/12* | (2006.01) |
| *A61B 90/50* | (2016.01) |
| *A61B 3/00* | (2006.01) |
| *A61B 3/10* | (2006.01) |
| *A61F 9/007* | (2006.01) |
| *A61B 90/00* | (2016.01) |
| *G02B 27/12* | (2006.01) |

(52) U.S. Cl.
CPC ......... *G02B 15/14* (2013.01); *G02B 21/0012* (2013.01); *G02B 21/22* (2013.01); *G02B 27/0025* (2013.01); *A61B 3/0075* (2013.01); *A61B 3/102* (2013.01); *A61B 3/12* (2013.01); *A61B 3/14* (2013.01); *A61B 2090/3616* (2016.02); *A61B 2090/3618* (2016.02); *A61B 2090/502* (2016.02); *G02B 27/126* (2013.01)

(58) Field of Classification Search
CPC .......... A61B 3/0075; A61B 2090/3616; A61B 2090/3618; A61B 2090/502; G02B 27/0025; G02B 27/126; G02B 15/04; G02B 15/14; G02B 21/0021; G02B 21/22
See application file for complete search history.

(56) References Cited

U.S. PATENT DOCUMENTS

| | | | | |
|---|---|---|---|---|
| 4,856,872 A * | 8/1989 | Spitznas | A61B 3/12 | 359/826 |
| 5,009,487 A * | 4/1991 | Reiner | G02B 17/04 | 359/376 |
| 5,282,085 A * | 1/1994 | Volkert | G02B 21/22 | 359/377 |
| 5,321,447 A * | 6/1994 | Sander | A61B 1/00195 | 351/205 |
| 5,706,073 A | 1/1998 | Volk | | |
| 5,886,812 A * | 3/1999 | Volk | A61B 3/125 | 359/368 |
| 6,019,472 A * | 2/2000 | Koester | A61B 3/125 | 351/219 |
| 6,212,006 B1 * | 4/2001 | Reiner | A61B 3/132 | 359/368 |
| 6,726,326 B2 * | 4/2004 | Fukuma | A61B 3/13 | 351/216 |
| 6,943,942 B2 * | 9/2005 | Horiguchi | G02B 21/0012 | 359/368 |
| 6,967,774 B2 * | 11/2005 | Kirchhuebel | A61B 3/13 | 351/219 |
| 7,085,046 B2 * | 8/2006 | Horiguchi | G02B 21/0012 | 359/368 |
| 7,387,385 B2 * | 6/2008 | Sander | G02B 21/0012 | 351/206 |
| 7,554,723 B2 * | 6/2009 | Moeller | G02B 21/0012 | 359/383 |
| 7,839,494 B2 * | 11/2010 | Reimer | A61B 3/102 | 356/73 |
| 8,049,873 B2 * | 11/2011 | Hauger | A61B 3/102 | 356/73 |
| 8,437,076 B2 * | 5/2013 | Takanashi | A61B 3/132 | 359/381 |
| 8,459,795 B2 * | 6/2013 | Seesselberg | A61B 3/1015 | 351/221 |
| 9,629,537 B2 * | 4/2017 | Matz | A61B 3/1225 | |
| 10,219,690 B2 * | 3/2019 | Manns | A61B 3/1015 | |
| 2002/0118448 A1 * | 8/2002 | Kirchhuebel | A61B 3/13 | 359/368 |
| 2003/0128333 A1 | 7/2003 | Fukuma et al. | | |
| 2003/0193647 A1 * | 10/2003 | Neal | A61B 3/103 | 351/221 |
| 2003/0214629 A1 | 11/2003 | Luloh et al. | | |
| 2004/0012760 A1 * | 1/2004 | Mihashi | A61B 3/107 | 351/205 |
| 2004/0089023 A1 * | 5/2004 | Hiraiwa | G02B 1/02 | 65/30.1 |
| 2004/0196432 A1 * | 10/2004 | Su | A61B 3/14 | 351/206 |
| 2004/0218266 A1 * | 11/2004 | Kirchhuebel | A61B 3/13 | 359/368 |
| 2005/0012992 A1 | 1/2005 | Kitajima | | |
| 2005/0128573 A1 * | 6/2005 | Merz | G02B 21/18 | 359/381 |
| 2005/0174655 A1 * | 8/2005 | Straehle | G02B 21/22 | 359/676 |
| 2008/0084540 A1 * | 4/2008 | Gaida | A61B 3/13 | 351/216 |
| 2008/0117432 A1 * | 5/2008 | Reimer | G01B 9/02035 | 356/511 |
| 2009/0021712 A1 * | 1/2009 | Kumazawa | G03F 7/70791 | 355/53 |
| 2009/0219483 A1 * | 9/2009 | Takanashi | A61B 3/132 | 351/205 |
| 2009/0279052 A1 * | 11/2009 | Hauger | A61B 3/13 | 351/208 |
| 2010/0265460 A1 * | 10/2010 | Mann | G02B 7/023 | 351/214 |
| 2011/0026035 A1 * | 2/2011 | Muto | A61B 3/102 | 356/456 |
| 2011/0194073 A1 * | 8/2011 | Sander | A61B 3/13 | 351/216 |
| 2011/0228218 A1 * | 9/2011 | Hauger | G01B 9/02004 | 351/205 |
| 2012/0184846 A1 * | 7/2012 | Izatt | A61B 3/132 | 600/425 |
| 2012/0238904 A1 * | 9/2012 | Manns | A61B 3/1015 | 600/558 |
| 2013/0057828 A1 * | 3/2013 | de Smet | A61B 3/12 | 351/207 |
| 2013/0083289 A1 * | 4/2013 | Hauger | A61B 3/18 | 351/221 |
| 2014/0340501 A1 * | 11/2014 | Hauger | A61B 90/20 | 348/79 |
| 2014/0362343 A1 * | 12/2014 | Hauger | G02B 21/16 | 351/206 |
| 2015/0119835 A1 * | 4/2015 | Seiwert | A61B 3/13 | 604/319 |
| 2015/0374233 A1 * | 12/2015 | Zhang | A61B 3/14 | 351/206 |
| 2016/0062111 A1 * | 3/2016 | Nobis | G02B 21/361 | 359/364 |
| 2016/0081545 A1 * | 3/2016 | Hauger | G01B 9/02035 | 351/221 |
| 2018/0125360 A1 * | 5/2018 | Hogele | G02B 15/04 | |

FOREIGN PATENT DOCUMENTS

| | | |
|---|---|---|
| DE | 10 2006 047 459 | 4/2008 |
| DE | 10 2008 011 608 | 9/2009 |
| DE | 10 2008 041 284 | 11/2009 |
| DE | 10 2010 001 853 | 8/2011 |
| EP | 2 316 330 | 5/2011 |
| WO | WO-2016-033952 | 3/2016 |

* cited by examiner

OPERATING MICROSCOPE

The present invention relates to an operating microscope for observing an eye and, in particular, an operating microscope for retinal surgery.

As a rule, operating microscopes for retinal surgery are used together with ophthalmoscopy magnifiers which facilitate the observation of the fundus of the eye using the operating microscope. Here, by means of the ophthalmoscopy magnifiers, there is a wide-angle observation, wherein the fundus or the retina is imaged on an intermediate image which then, in turn, is observed using the operating microscope. A wide-angle observation of the fundus or the retina would not be possible without the ophthalmoscopy magnifier. Ophthalmoscopy magnifiers are often arranged on pivoting apparatuses, by means of which they are connected to the operating microscope in such a way that they can be pivoted into the observation beam path of the operating microscope. Ophthalmoscopy magnifiers and operating microscopes having ophthalmoscopy magnifiers are described in, for example, DE 35 39 009 A1, DE 10 2006 047 459 A1, DE 10 2010 001 853 A1, EP 2 316 330 B1, U.S. Pat. Nos. 4,786,161, 5,321,447, 5,706,073, US 2003/0214629 A1, US 2005/0012992 A1 and WO 2016/033952 A1.

In DE 10 2010 001 853 A1 and U.S. Pat. No. 5,321,447, the ophthalmoscopy magnifiers are integrated in an attachment module for an operating microscope. In addition to the ophthalmoscopy magnifier, the attachment module comprises a lens that is displaceable along the optical axis and situated between the intermediate image and the main objective of the operating microscope when the attachment module is attached to the operating microscope. The displaceable lens allows focusing on different regions of the eye.

In DE 35 39 009 A1 too, the ophthalmoscopy magnifier is part of an attachment module for an operating microscope. In addition to the ophthalmoscopy magnifier, the attachment module also comprises a further lens which is arranged between the intermediate image and the main objective of the operating microscope. By means of this lens, which is situated in the vicinity of the intermediate image, the aperture is matched to the aperture of the main objective of the operating microscope.

The described combinations of operating microscope and ophthalmoscopy magnifier often have the disadvantage of a non-ideal image quality. Here, the non-ideal image quality results from the image quickly reaching the diffraction limit. A further cause of the non-ideal image quality lies in the fact that ophthalmoscopy magnifiers with high refractive powers are often embodied as single lenses, which lead to relatively large aberrations.

Therefore, in relation to this prior art, it is an object of the present invention to provide an operating microscope having a fundus imaging system that comprises an ophthalmoscopy magnifier, by means of which a high image quality is obtainable.

This object is achieved by means of an operating microscope as claimed in claim 1. The dependent claims contain advantageous configurations of the invention.

An operating microscope according to the invention for observing an eye comprises a main objective and a fundus imaging system that is positionable in the beam path between the eye and the main objective. Here, the fundus imaging system is provided with an ophthalmoscopy magnifier. In the operating microscope according to the invention, the main objective has a focal length in the range between 90 and 160 mm, in particular between 100 and 150 mm and further particularly between 100 mm and 135 mm.

By reducing the focal length of the main objective to a focal length in the range between 90 and 160 mm, in particular between 100 and 150 mm and further particularly between 100 and 135 mm, it is reduced by a factor in the range between approximately 1.25 and 2.2, in particular between 1.3 and 2 and further particularly between 1.5 and 2 in relation to the usual focal length of a main objective of 200 mm. As a result, this increases the imaging scale with which the aperture stops or the optical elements acting as aperture stops in the stereoscopic partial beam paths are imaged onto the plane of the eye pupil of the eye to be examined. The images of the aperture stops or of the optical elements acting as aperture stops situated in the plane of the eye pupil define the entry pupil for the optical system made of eye lens, fundus imaging system and main objective, said entry pupil, in turn, setting the aperture angle of a beam emanating from the observed retina and consequently being incorporated in the numerical aperture of the aforementioned optical system. By increasing the entry pupil there is an increase in the numerical aperture of the optical system made of eye lens, fundus imaging system and operating microscope, and so the resolution capability of this system is increased. As a result of this increase in the resolution capability, the system does not reach the diffraction limit as quickly, and so the optical quality of the image is improved.

In particular, the operating microscope can be configured as a digital operating microscope having at least one digital image sensor, as a result of which the installation height of the microscope may be reduced. Then, the operating microscope can be equipped with a software module or hardware module for digital magnification of the image recorded by means of the image sensor. As a result of the image recorded by the digital image sensor having a higher resolution in comparison with an operating microscope with a standard main objective, which has a focal length of 200 mm, the image recorded by the digital image sensor offers more play for digital post-magnification.

Additionally, or alternatively, the fundus imaging system of the operating microscope according to the invention comprises an optics group, the dispersion properties of which are matched to the dispersion properties of the ophthalmoscopy magnifier in such a way that it compensates a chromatic aberration, in particular the transverse chromatic aberration, of the ophthalmoscopy magnifier. The ophthalmoscopy magnifier typically consists of only one glass type, the dispersion properties of which cause the chromatic aberration. Both a longitudinal chromatic aberration, which is caused by different focal lengths for different wavelengths, and the transverse chromatic aberration, which can be traced back to a different imaging scale of the ophthalmoscopy magnifier for different wavelengths, arise in the process. The transverse chromatic aberration leads to the images at different wavelengths having different sizes in the intermediate image plane, with this effect increasing in the image field with increasing distance from the optical axis. The transverse chromatic aberration partly also is a consequence of the longitudinal chromatic aberration, which increases with increasing pupil dimension. The chromatic aberration and, in particular, the transverse chromatic aberration can therefore at least partly counteract the increase in image quality gained by increasing the entry pupil. The full advantage of the larger entry pupil therefore only can be obtained in conjunction with the optics group that compensates the chromatic aberration. However, even without increasing the entry pupil, the compensation of the chromatic aberration, in particular of the transverse chromatic aberration, increases the imaging quality.

The ophthalmoscopy magnifier forms an intermediate image that is situated between the ophthalmoscopy magnifier and the main objective. The optics group is particularly effective at compensating the chromatic aberration if it is arranged between the intermediate image and the main objective, in particular if it is arranged closer to the intermediate image than the main objective. Here, the distance between the optics group and the main objective is preferably at least 1.5 times and, in particular, at least 2.5 times the distance between the optics group and the intermediate image.

In a particular configuration of the operating microscope according to the invention, the main objective can be a varioscope objective, the focal length of which can vary between 90 and 160 mm, in particular between 100 and 150 mm and further particularly between 100 mm and 135 mm. The use of a varioscope objective as a main objective facilitates focusing onto different spatial orientations of the intermediate images that vary over a large range. By way of example, the spatial orientation of the intermediate image varies in relation to an eye without a refractive error and that is not detuned in the case of near-sighted and long-sighted patient eyes, and also in the case of strongly detuned patient eyes, for example in the case of patient eyes filled with viscoelastic or air for applicative reasons. By means of the varioscope objective, it is possible to focus the operating microscope to the different spatial orientations of the intermediate images, and so a sharp fundus image can be generated in all situations. Moreover, the option of equipping the fundus imaging system with at least two interchangeable ophthalmoscopy magnifiers exists in this configuration of the operating microscope. Different ophthalmoscopy magnifiers typically have different spatial orientations of their intermediate images, onto which it is possible to focus in each case by adjusting the varioscope objective.

In a further configuration of the operating microscope according to the invention, the latter may comprise an OCT section (OCT: optical coherence tomography). Additional depth information in relation to the observed structures can be obtained and added to the image with the aid of the OCT section, particularly if the operating microscope is embodied as a digital operating microscope. Moreover, the OCT section can be used to keep the distance between the patient eye and optics ideal or to adjust this distance ideally. To this end, the fundus imaging system may comprise a distance adjustment system for adjusting the distance of the ophthalmoscopy magnifier. This distance adjustment system may be a manual distance adjustment system. However, if the distance adjustment system comprises a motor for motor-controlled adjustment of the distance between the ophthalmoscopy magnifier and the eye, a control unit that is connected to the motor and the OCT section may be present. Said control unit then is embodied to ascertain the distance between the operating microscope and the fundus from an OCT signal obtained with the aid of the OCT section to adjust the distance between the ophthalmoscopy magnifier and the eye on the basis of the ascertained distance between the operating microscope and the fundus. In this way, an automatic adjustment of the suitable distance between the ophthalmoscopy magnifier and the eye is rendered possible. Moreover, the ideal distance also may be maintained within the scope of a closed-loop control. Adjusting and/or holding the ideal distance ensures that the image quality does not suffer on account of an incorrectly adjusted distance.

Further features, properties and advantages of the present invention will become apparent from the following description of exemplary embodiments with reference to the accompanying figures.

FIG. 1 shows a schematic illustration of the structure of an operating microscope having an optical eyepiece.

FIG. 2 schematically shows the basic structure of a varioscope objective.

The basic structure of the operating microscope 2 is explained below with reference to FIG. 1.

Figure 1:
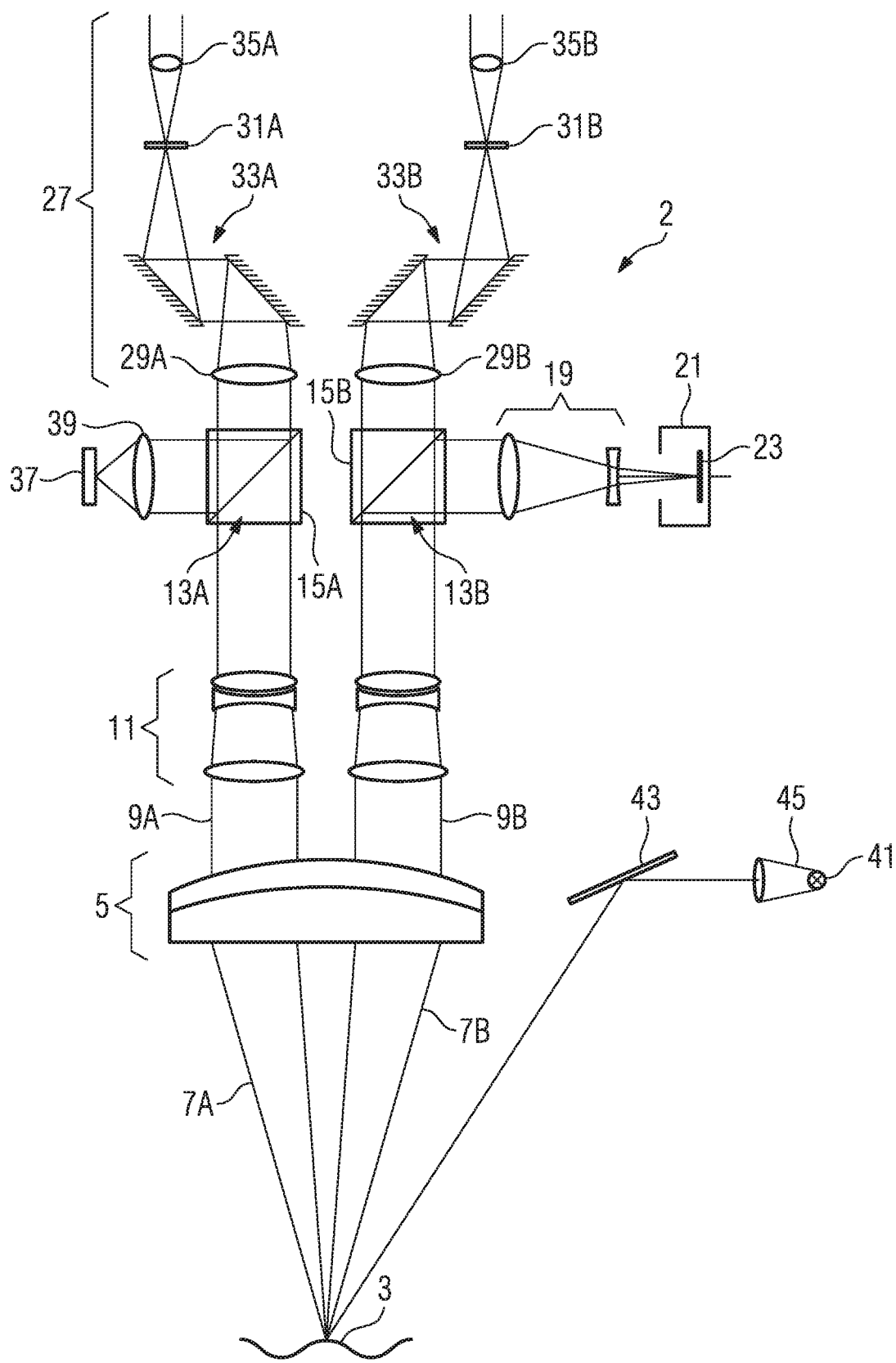

The operating microscope 2 shown in FIG. 1 comprises, as essential components, an objective 5 that should face an object field 3, said objective, in particular, being able to be embodied as an achromatic or apochromatic objective. In the present exemplary embodiment, the objective 5 consists of two partial lenses that are cemented to one another and form an achromatic objective. The object field 3 is arranged in the focal plane of the objective 5 such that it is imaged at infinity by the objective 5. Expressed differently, a divergent beam 7 emanating from the object field 3 is converted into a parallel beam 9 during its passage through the objective 5.

A magnification changer 11 is arranged on the observer side of the objective 5, which magnification changer can be embodied either as a zoom system for changing the magnification factor in a continuously variable manner as in the illustrated exemplary embodiment, or as a so-called Galilean changer for changing the magnification factor in a stepwise manner. In a zoom system, constructed by way of example from a lens combination having three lenses, the two object-side lenses can be displaced in order to vary the magnification factor. In actual fact, however, the zoom system also can have more than three lenses, for example four or more lenses, in which case the outer lenses then can be arranged in a fixed manner. In a Galilean changer, by contrast, there are a plurality of fixed lens combinations which represent different magnification factors and which can be introduced into the beam path alternately. Both a zoom system and a Galilean changer convert an object-side parallel beam into an observer-side parallel beam having a different beam diameter. In the present exemplary embodiment, the magnification changer 11 already is part of the binocular beam path of the operating microscope 1, i.e. it has a dedicated lens combination for each stereoscopic partial beam path 9A, 9B of the operating microscope 1. In the present exemplary embodiment, a magnification factor is adjusted by means of the magnification changer 11 by way of a motor-driven actuator which, together with the magnification changer 11, is part of a magnification changing unit for adjusting the magnification factor.

In the present example, the magnification changer 11 is adjoined on the observer side by an interface arrangement 13A, 13B, by means of which external devices can be connected to the operating microscope 1 and which comprises beam splitter prisms 15A, 15B in the present exemplary embodiment. However, in principle, use can also be made of other types of beam splitters, for example partly transmissive mirrors. In the present exemplary embodiment, the interfaces 13A, 13B serve to output couple a beam from the beam path of the operating microscope 2 (beam splitter prism 15B) and to input couple a beam into the beam path of the operating microscope 2 (beam splitter prism 15A).

In the present exemplary embodiment, the beam splitter prism 15A in the partial beam path 9A serves to mirror information or data for an observer into the partial beam path 9A of the operating microscope 1 with the aid of a display 37, for example a digital mirror device (DMD) or an LCD display, and an associated optical unit 39 by means of the beam splitter prism 15A. A camera adapter 19 with a camera 21 fastened thereto, said camera being equipped with an electronic image sensor 23, for example with a CCD sensor or a CMOS sensor, is arranged at the interface 13B in the other partial beam path 9B. By means of the camera 21, it is possible to record an electronic image and, in particular, a digital image of the tissue region 3. In particular, a hyperspectral sensor also can find use as an image sensor, said hyperspectral sensor having not only three spectral channels (e.g. red, green and blue) but a multiplicity of spectral channels.

In the present example, a binocular tube 27 adjoins the interface 13 on the observer side. It has two tube objectives 29A, 29B, which focus the respective parallel beam 9A, 9B onto an intermediate image plane 31, i.e. image the observation object 3 onto the respective intermediate image plane 31A, 31B. The intermediate images situated in the intermediate image planes 31A, 31B are finally imaged at infinity in turn by eyepiece lenses 35A, 35B, such that an observer can observe the intermediate image with a relaxed eye. Moreover, an increase in the distance between the two partial beams 9A, 9B is effectuated in the binocular tube by means of a mirror system or by means of prisms 33A, 33B in order to adapt said distance to the intraocular distance of the observer. In addition, image erection is carried out by the mirror system or the prisms 33A, 33B.

The operating microscope 2 moreover is equipped with an illumination apparatus, by means of which the object field 3 can be illuminated with broadband illumination light. To this end, the illumination apparatus has a white-light source 41, for example a halogen lamp or a gas discharge lamp, in the present example. The light emanating from the white-light source 41 is directed in the direction of the object field 3 via a deflection mirror 43 or a deflection prism in order to illuminate said field. Furthermore, an illumination optical unit 45 is present in the illumination apparatus, said illumination optical unit ensuring uniform illumination of the entire observed object field 3.

Reference is made to the fact that the illumination beam path illustrated in FIG. 1 is very schematic and does not necessarily reproduce the actual course of the illumination beam path. In principle, the illumination beam path can be embodied as a so-called oblique illumination, which comes closest to the schematic illustration in FIG. 1. In such oblique illumination, the beam path extends at a relatively large angle (6° or more) with respect to the optical axis of the objective 5 and, as illustrated in FIG. 1, may extend completely outside the objective. Alternatively, however, there is also the possibility of allowing the illumination beam path of the oblique illumination to extend through a marginal region of the objective 5. A further option for the arrangement of the illumination beam path is the so-called 0° illumination, in which the illumination beam path extends through the objective 5 and is input coupled into the objective between the two partial beam paths 9A, 9B, along the optical axis of the objective 5 in the direction of the object field 3. Finally, it is also possible to embody the illumination beam path as a so-called coaxial illumination, in which a first illumination partial beam path and a second illumination partial beam path are present. The illumination partial beam paths are input coupled into the operating microscope in a manner parallel to the optical axes of the observation partial beam paths 9A, 9B by way of one or more beam splitters such that the illumination extends coaxially in relation to the two observation partial beam paths.

In the embodiment variant of the operating microscope 2 shown in FIG. 1, the objective 5 only consists of an achromatic lens with a fixed focal length. However, use can also be made of an objective lens system made of a plurality of lenses, in particular a so-called varioscope objective, by means of which it is possible to vary the working distance of the operating microscope 2, i.e. the distance between the object-side focal plane and the vertex of the first object-side lens surface of the objective 5, also referred to as front focal distance. The object field 3 arranged in the focal plane is imaged at infinity by the varioscope objective 50, too, and so a parallel beam is present on the observer side.

Figure 2:
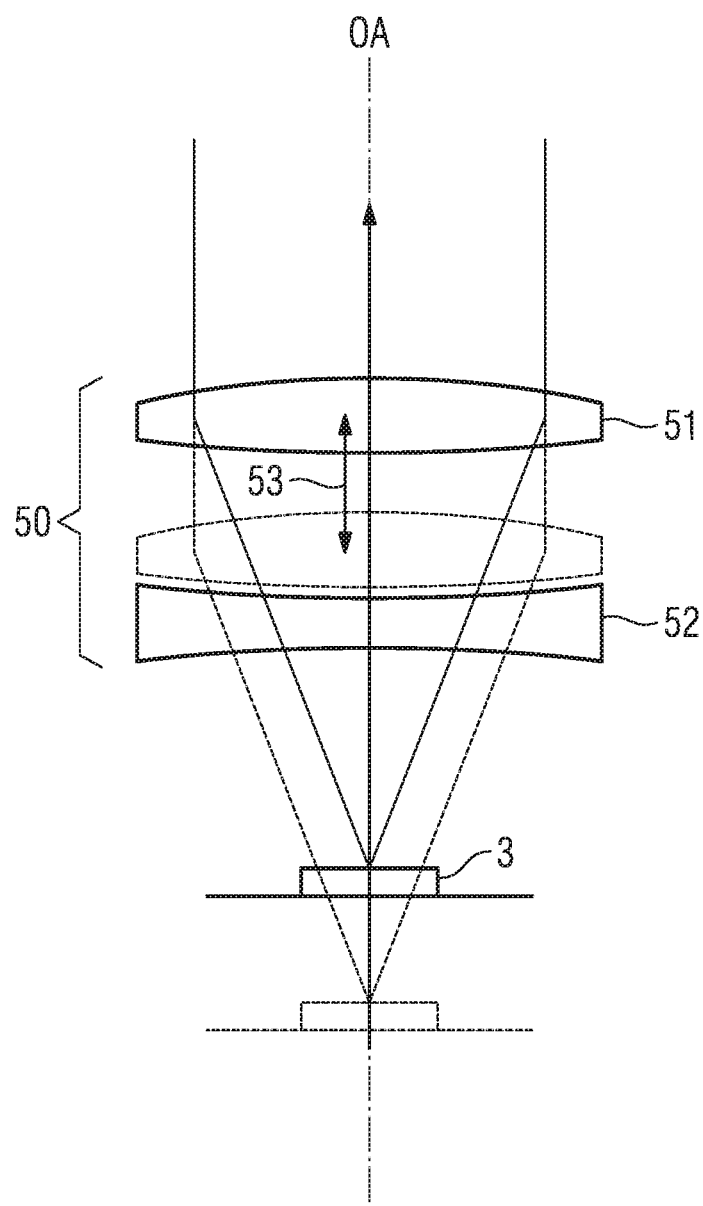

One example of a varioscope objective is illustrated schematically in FIG. 2. The varioscope objective 50 comprises a positive member 51, i.e. an optical element having positive refractive power, which is schematically illustrated as a convex lens in FIG. 2. Moreover, the varioscope objective 50 comprises a negative member 52, i.e. an optical element having negative refractive power, which is schematically illustrated as a concave lens in FIG. 2. The negative member 52 is situated between the positive member 51 and the object field 3. In the illustrated varioscope objective 50, the negative member 52 has a fixed arrangement, whereas, as indicated by the double-headed arrow 53, the positive member 51 is arranged to be displaceable along the optical axis OA. When the positive member 51 is displaced into the position illustrated by dashed lines in FIG. 2, the back focal length increases, and so there is a change in the working distance of the operating microscope 2 from the object field 3.

Even though the positive member 51 has a displaceable configuration in FIG. 2, it is also possible, in principle, to arrange the negative member 52 to be movable along the optical axis OA instead of the positive member 51. However, the negative member 52 often forms the last lens of the varioscope objective 50. A stationary negative member 52 therefore offers the advantage of making it easier to seal the interior of the operating microscope 2 from external influences. Furthermore, it is noted that, even though the positive member 51 and the negative member 52 in FIG. 2 are only illustrated as individual lenses, each of these members may also be realized in the form of a lens group or a cemented element instead of in the form of an individual lens, e.g. in order to embody the varioscope objective to be achromatic or apochromatic.

Figure 3:
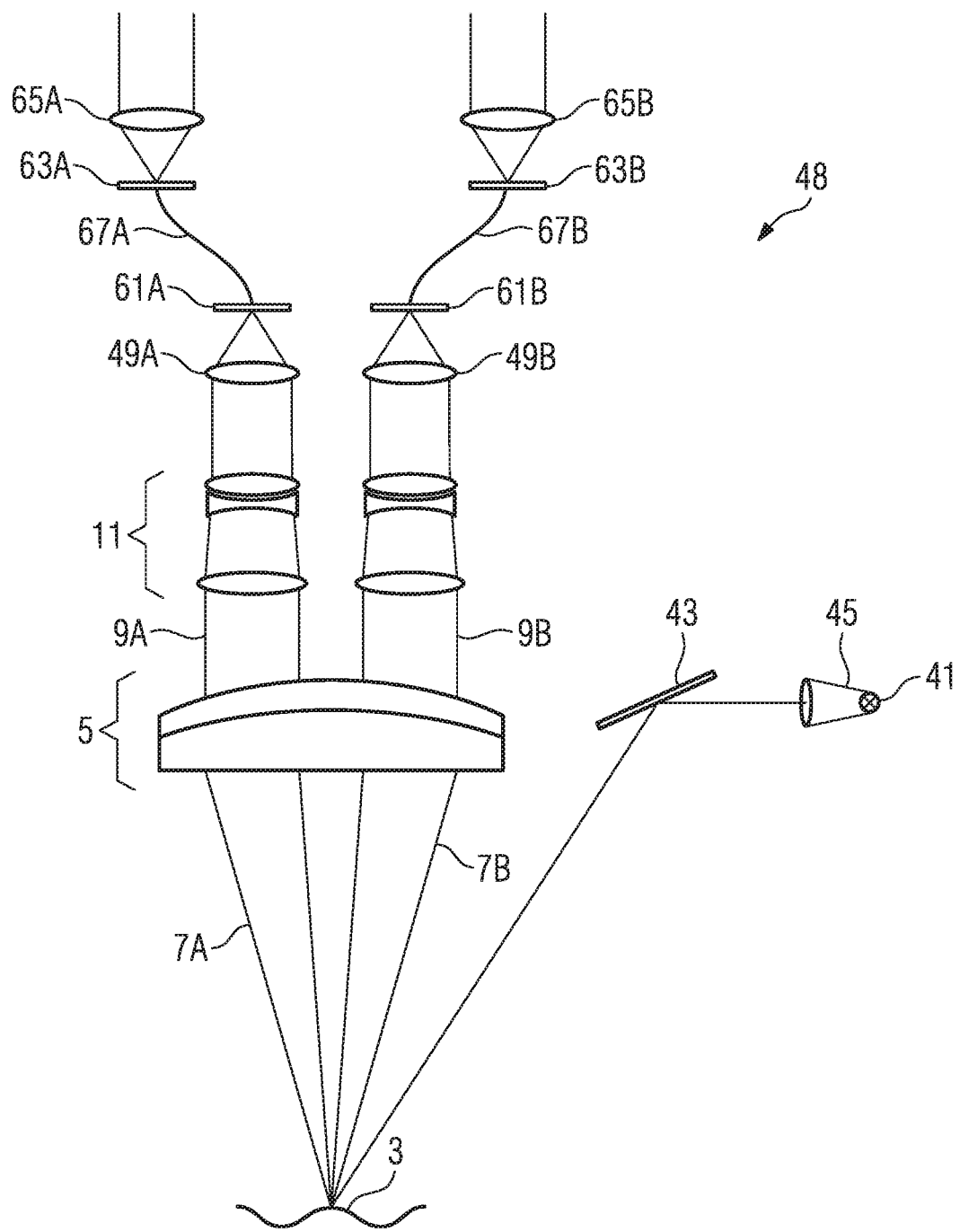
FIG. 3 shows a schematic illustration of a digital operating microscope.

FIG. 3 shows a schematic illustration of an example of a digital operating microscope 48. In this operating microscope, the main objective 5, the magnification changer 11 and the illumination system 41, 43, 45 do not differ from the operating microscope 2 with the optical eyepiece that is illustrated in FIG. 1. The difference lies in the fact that the operating microscope 48 shown in FIG. 3 does not comprise an optical binocular tube. Instead of the tube objectives 29A, 29B from FIG. 1, the operating microscope 48 from FIG. 3 comprises focusing lenses 49A, 49B, by means of which the binocular observation beam paths 9A, 9B are imaged onto digital image sensors 61A, 61B. Here, the digital image sensors 61A, 61B can be e.g. CCD sensors or CMOS sensors. The images recorded by the image sensors 61A, 61B are transmitted digitally to digital displays 63A, 63B, which may be embodied as LED displays, as LCD displays or as displays based on organic light-emitting diodes (OLEDs). Like in the present example, eyepiece lenses 65A, 65B can be assigned to the displays 63A, 63B, by means of which the images displayed on the displays 63A, 63B are imaged at infinity such that an observer can observe said images with relaxed eyes. The displays 63A, 63B and the eyepiece lenses 65A, 65B can be part of a digital binocular tube; however, they can also be part of a head-mounted display (HMD) such as e.g. a pair of smartglasses.

Even though FIG. 3, like FIG. 1, only illustrates an achromatic lens 5 with a fixed focal length, the operating microscope 48 shown in FIG. 3 may comprise a varioscope objective instead of the objective lens 5, like the operating microscope 2 illustrated in FIG. 1. Furthermore, FIG. 3 shows a transfer of the images recorded by the image sensors 61A, 61B to the displays 63A, 63B by means of cables 67A, 67B. However, instead of in a wired manner, the images can also be transferred wirelessly to the displays 63A, 63B, especially if the displays 63A, 63B are part of a head-mounted display.

Figure 4:
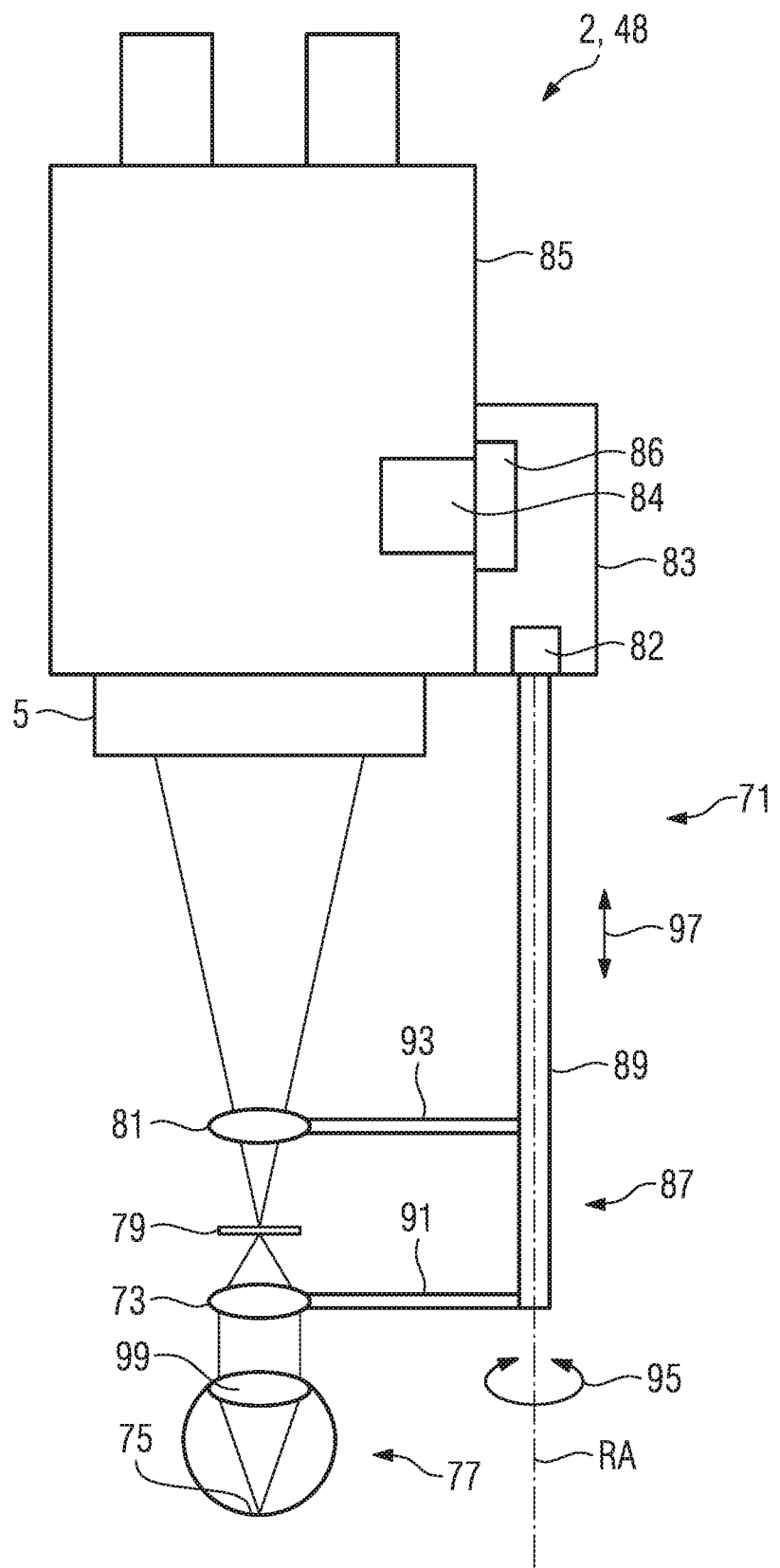
FIG. 4 shows an operating microscope with a fundus imaging system.

FIG. 4 shows an operating microscope 2, 48, on which a fundus imaging system 71 has been arranged. The operating microscope 2, 48 can be embodied as an operating microscope 2 with an optical eyepiece or as an operating microscope 48 with a digital eyepiece.

The fundus imaging system comprises an ophthalmoscopy magnifier 73, by means of which the fundus 75 of an eye 77 is imaged into an intermediate image plane 79. Further, the fundus imaging system 71 comprises an optics group 81, which is arranged between the intermediate image plane 79 and the main objective 5 of the operating microscope. Here, in the present exemplary embodiment, the distance between the optics group 81 and the main objective 5 is greater than the distance between the optics group 81 and the intermediate image plane 79, and so the optics group 81 is positioned closer to the intermediate image 79 than to the main objective 5. Here, the distance between the optics group 81 and the main objective 5 can correspond to, in particular, at least 1.5 times and preferably at least 2.5 times the distance between the optics group 81 and the intermediate image plane 79.

The fundus imaging system 71 is fastened to the operating microscope 2, 48 by means of a fastening system. In the present exemplary embodiment, the latter comprises an anchoring element 83 for anchoring the fundus imaging system 71 on the main body 85 of the operating microscope 2, 48 and a pivoting system 87 for pivoting the ophthalmoscopy magnifier 73 and the optics group 81 into the observation beam path between the eye 77 and the main objective 5. In the present exemplary embodiment, the pivoting system comprises a shaft 89 or a shaft-like structure which can be rotated about an axis of rotation RA by means of a motor 82 arranged in the anchoring element 83. As a result of the rotation, the ophthalmoscopy magnifier 73 and optics group 81, which are fastened, respectively, by means of an ophthalmoscopy magnifier holder 91 and by means of an optics group holder 93, can be pivoted into or out of the observation beam path. The pivoting process is indicated in FIG. 4 by the double-headed arrow 95. Moreover, the anchoring means 83 comprise a further motor 86 in the present exemplary embodiment, by means of which the shaft or shaft-like structure 89 can be displaced along the optical axis RA in order to position the ophthalmoscopy magnifier 73 in such a way that a suitably focused intermediate image arises. The displacement of the shaft or shaft-like structure 89 with the ophthalmoscopy magnifier 73 that is fastened thereon and the optics group 81 that likewise is fastened to the shaft or shaft-like structure 89 is indicated by the double-headed arrow 97 in FIG. 4.

Compared to a standard main objective, the main objective of the operating microscope 2, 48 illustrated in FIG. 4 has a focal length that is reduced by a factor of 1.5 to 2. In the case of an otherwise usual focal length of 200 mm for the main objective 5, the operating microscope 2, 48 in FIG. 4 thus has a focal length in the range between 100 mm and approximately 135 mm. If the main objective 5 is a varioscope objective, the focal length thereof can be varied in the range between 100 mm and 135 mm. In other variants to the illustrated embodiment variant, the focal length can lie or be varied in the range between 100 mm and 150 mm or even in the range between 90 and 160 mm. As a result of reducing the focal length of the main objective 5, there is an increase in the entry pupil, i.e. the object-side image of the aperture stop or of the optical element of the operating microscope 2, 48 acting as an aperture stop, by the same factor by which the focal length has been reduced in relation to the usual focal values. Thus, in the case of a focal length reduction by a factor of 2, the diameter of the entry pupil likewise increases by a factor of 2 and if the focal length is reduced by a factor of 1.5, the diameter of the entry pupil increases by a factor of 1.5. Since the entry pupil is situated in the region of the eye pupil 99 when using the operating microscope 2, 48 that has been equipped with the fundus imaging system 71 and since the eye pupil 99 represents the first lens for the optical system for imaging the fundus 75, the numerical aperture of the beam entering the eye lens 99 determines the resolution of the system. There is an increase in the numerical aperture by increasing the pupil diameter; this is accompanied by an increased resolution. As a result of reducing the objective focal length of the main objective 5 of the operating microscope 2, 48 and the increase in the diameter of the entry pupil accompanied thereby, the resolution of the fundus imaging is improved to such an extent that the diffraction limit of the system is not reached as quickly during magnified observation of the fundus as in the case when an operating microscope having a main objective 5 that has the standard focal length is used.

By increasing the entry pupil, there is also an increase in the diameter of the beam passing through the ophthalmoscopy magnifier 73. However, the ophthalmoscopy magnifier 73 is only produced from a single glass material (mineral or organic), and so the imaging thereof inherently has a corresponding chromatic aberration. As a result of this, a longitudinal chromatic aberration and a transverse chromatic aberration arise. The longitudinal chromatic aberration increases with the increase in the entry pupil and the magnification of the beam entering into the ophthalmoscopy magnifier 73 accompanying the latter; this also leads to an increase in the transverse chromatic aberration. The increased longitudinal chromatic aberration and, in particular, the increased transverse chromatic aberration reduce the imaging quality and thus cancel again some of the imaging quality obtained by the increased resolution. The optics group 81 serves to compensate the increased chromatic aberration, in particular the increased transverse chromatic aberration. To this end, it is advantageous if the optics group 81 is arranged in the vicinity of the intermediate image plane 79—but not in the intermediate image plane 79—like in the present exemplary embodiment. In this way, it is possible to keep the diameter of the optics group small, which firstly reduces the production costs and secondly helps avoid the introduction of further aberrations.

Figure 5:
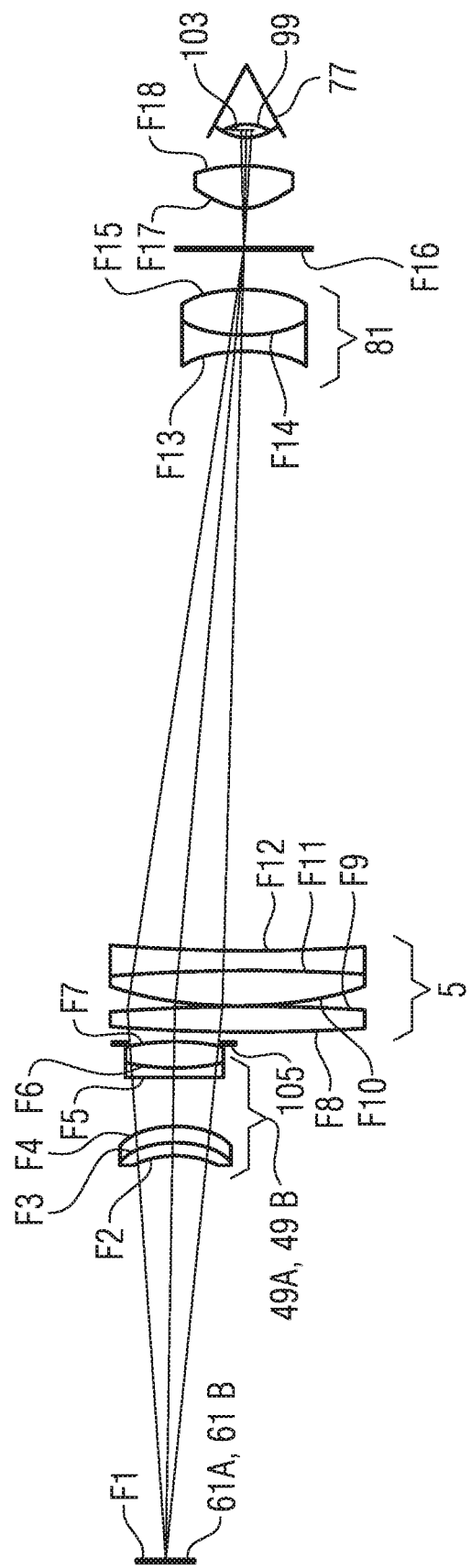
FIG. 5 shows the optical components of the operating microscope and of the fundus imaging system from FIG. 4.

FIG. 5 shows the optical components of a specific exemplary embodiment for a digital operating microscope 48 having a fundus imaging system 71 according to the invention. In the specific exemplary embodiment, the operating microscope itself only comprises as optical components the main objective 5 and a camera objective, which serves as a focusing lens 49 for focusing the beam path onto the digital image sensor 61. This example does not contain a magnification changer. Instead, there can be, without problems, a digital magnification of the digital image in the present exemplary embodiment on account of the increased resolution. In the exemplary embodiment, the main objective 5 is embodied as an apochromatic lens having a cemented element and an individual lens in order to ensure the color purity of the main objective. In the present exemplary embodiment, the camera objective has a two-lens embodiment, with each of the lenses consisting of a two-part cemented element. The optics group 81 of the fundus imaging system is also embodied as a cemented element and the ophthalmoscopy magnifier 29 is a rotationally symmetric aspherical individual lens, in which the aspherical surface faces away from the eye 77. FIG. 5 likewise illustrates the entry pupil 103 which, as already mentioned previously, represents the object-side image of the aperture stop 105 that is embodied as a physical stop in the present exemplary embodiment. Here, the optics group 81 only serves to correct the aberration and not to modify the aperture of the observation beam passing therethrough.

The optical parameters of the surfaces F1 to F18 shown in FIG. 5 are compiled in the following table.

group 81 and the ophthalmoscopy magnifier 73, which are shared with the observation beam path. Moreover, the OCT section comprises the outlet end of an optical fiber 107 as a light source, a collimator optical unit 109, a scanning mirror 111, a beam widening optical unit 113 and a deflection mirror 115. White light, which is generated by a white-light source (not depicted here) and guided to the OCT section by the optical fiber, emerges from the outlet end of the optical fiber 107. From the divergent beam emerging from the outlet end of the optical fiber 107, the collimator optical unit 109 forms a parallel (collimated) beam which is subsequently widened by means of the beam widening optical unit 113 and, in this way, deflected by means of the deflection mirror 115 in the direction of the main objective 5. Then, the beam is focused onto the intermediate image plane 79 by the main objective. With the aid of the scanning mirror 111 arranged between the collimator optical unit 109 and the beam widening optical unit 113, it is possible to displace the position of the focal spot in the intermediate image plane 79. In the present exemplary embodiment, the scanning mirror 111 is embodied as a MEMS mirror, i.e. as a mirror that can be rotated about an axis lying in the mirror plane by means of a MEMS (micro-electromechanical system) oscillator. If a two-dimensional scanning is intended to be realized, a second MEMS oscillator may be present, by means of which the scanning mirror can be rotated about a second axis of rotation that likewise lies within the mirror plane. Here, the two axes of rotation are not parallel and preferably extend at an angle of 90° in relation to one another.

| Surface | Radius [mm] | Thickness [mm] | Aperture radius [mm] | Glass | Refractive index at $\lambda =$ 546.074 nm | Abbe number at $\lambda =$ 546.074 nm |
| --- | --- | --- | --- | --- | --- | --- |
| F1 | inf | 66.35 | 5 | AIR | | |
| F2 | −11.8 | 2 | 6 | N-LAK8 | 1.71616 | 53.61 |
| F3 | −14.2 | 3.1 | 8 | S-FPL51 | 1.49845 | 81.51 |
| F4 | −14.2 | 7.97 | 8 | AIR | | |
| F5 | 220 | 1.8 | 8 | N-KZFS4 | 1.61664 | 44.27 |
| F6 | 34.43 | 4 | 8 | S-FPL51 | 1.49845 | 81.51 |
| F7 | −40 | 2 | 8 | AIR | | |
| F8 | 182.3 | 4 | 20 | S-FPL51 | 1.49845 | 81.51 |
| F9 | −182.3 | 0.2 | 20 | AIR | | |
| F10 | 67 | 6 | 20 | S-FPL51 | 1.49845 | 81.51 |
| F11 | −200 | 3 | 20 | S-NBH8 | 1.72538 | 34.47 |
| F12 | 200 | 99.635833 | 20 | AIR | | |
| F13 | −22 | 2.5 | 10 | N-SK5 | 1.59142 | 61 |
| F14 | 19 | 7.5 | 10 | N-SF1 | 1.72308 | 29.39 |
| F15 | −22 | 5.824031 | 10 | AIR | | |
| F16 | inf | 7.9 | 7 | AIR | | |
| F17 | 7.311244 | 7 | 8 | N-SK5 | 1.59142 | 61 |
| F18 | −20.097 | 5.848164 | 8 | AIR | | |

The surface F17 is a rotationally symmetric aspherical surface having the following coefficients:
CC 0
AS2 −1.94E-04
AS3 4.50E-07
AS4 −1.35E-08
AS5 9.02E-11

In order to ensure an optical quality of the fundus imaging, an ideal distance should be maintained between the patient eye and the optical unit. To this end, the operating microscope according to the invention has an OCT section in an advantageous development, said OCT section allowing a very accurate determination of the distance. This OCT section comprises, inter alia, the main objective 5, the optics For closed-loop control of the distance between the optical unit and the fundus, the OCT section can be connected to a control unit 84 (cf. FIG. 4) which regulates this distance to the ideal distance by means of the motor 86 in the anchoring element. As a result, an unchanging good imaging quality can be ensured.

Figure 6:
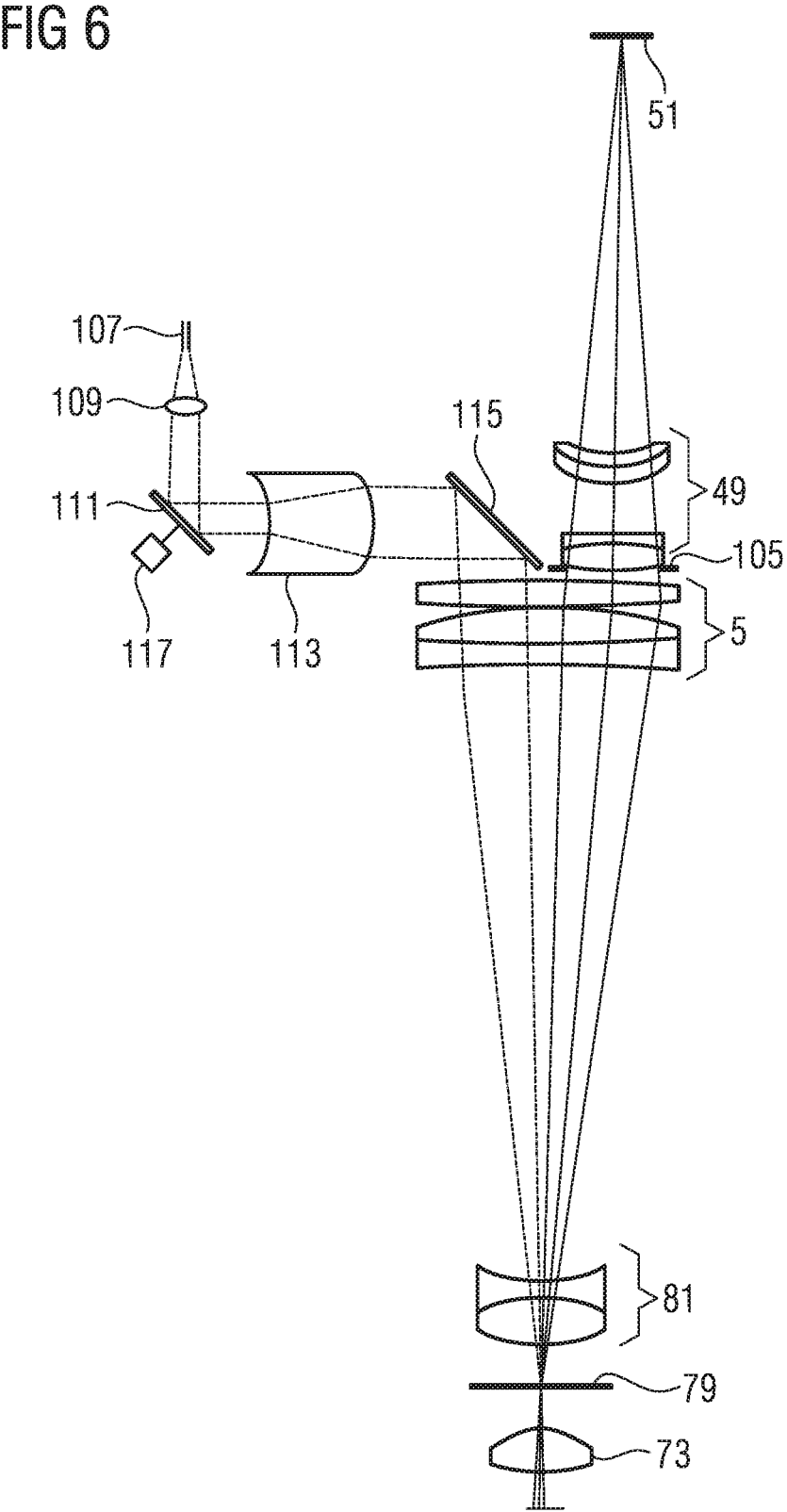
FIG. 6 shows the optical components from FIG. 5 with an additional OCT section.

In contrast to the OCT section illustrated in FIG. 6, the latter can be provided with optical elements that are displaceable along the optical axis of the section in order to be able to vary the focal length of the section.

In addition to maintaining the ideal distance for the fundus imaging, the OCT section can also find use intraoperatively by generating depth information for the observed fundus structures.

By way of example, an operating microscope 2, 48 according to the invention, having a fundus imaging system 71 as described on the basis of the exemplary embodiments, can find use within the scope of retinal surgery. Then, during the preparation of the operation, the system can be focused onto a plane in the region of the anterior section of the patient eye 77 instead of on the fundus 75 by removing the ophthalmoscopy magnifier 73 and the optics group 81 that is close to the intermediate image from the beam path (by pivoting out in the present exemplary embodiment). Then, the main objective 5 is focused on the anterior section of the eye 77. If the main objective 5 is a varioscope objective, the focusing can be effectuated by means of internal focusing, i.e. the focusing is effectuated by displacing the lenses of the varioscope objective relative to one another. If the objective is an objective with a fixed focal length, the focusing can be undertaken by means of external focusing, i.e. the entire operating microscope 2, 48 is displaced along the optical axis of the main objective 5 for focusing purposes.

Only one ophthalmoscopy magnifier 73 was respectively present in the described exemplary embodiments of the operating microscope 2, 48 with the fundus imaging system 71. However, sometimes it can be advantageous if it is possible to change between ophthalmoscopy magnifiers with different properties. To this end, the fundus imaging system 71 may comprise at least two ophthalmoscopy magnifiers, which can be interchanged. In this case, the holder 91 for the ophthalmoscopy magnifier is equipped with a changing organism which allows the available ophthalmoscopy magnifiers to be interchanged.

The operating microscope according to the invention facilitates high quality imaging of the fundus. The improved resolution by increasing the entry pupil predominantly contributes to the improved imaging quality. Moreover, the correction of the chromatic aberration, in particular of the transverse chromatic aberration, with the aid of the optics group close to the intermediate image makes an important contribution to ensuring a high image quality. Additionally, the OCT section can also help to ensure a high image quality as it facilitates an exact ascertainment of the distance from the observed structure and thereby simplifies the adjustment and possibly holding of the exact focal distance.

The present invention has been described in detail on the basis of exemplary embodiments for explanation purposes. A person skilled in the art recognizes, however, that deviations from the exemplary embodiments described are possible. Some possible deviations were already specified in the exemplary embodiments. However, further deviations are possible. Thus, for example, a sterile (often plane parallel) optically transparent element (often made of a plastic) may be present between the eye pupil 99 and the ophthalmoscopy magnifier 73. By way of example, this element can be a sterile termination glass of a drape. The sterile optically transparent element can be assembled from one or more optical elements and can have no refractive power or a refractive power that differs from zero. By way of example, it can be fastened to the holder 91 for the ophthalmoscopy magnifier. Moreover, it is possible to provide a device for digital post-magnification of the digital image of the fundus in order to make the details more easily identifiable. Therefore, the present invention is not intended to be restricted to the specific exemplary embodiments, but rather only by the appended claims.

LIST OF REFERENCE SIGNS

49A,B Focusing lens
61A,B Digital image sensor
63A,B Digital display
65A,B Eyepiece lens
67A,B Cable
71 Fundus imaging system
73 Ophthalmoscopy magnifier
75 Fundus
77 Eye
79 Intermediate image plane
81 Optics group
82 Motor
83 Anchoring element
84 Control unit
86 Main body
87 Motor
91 Pivoting system
93 Shaft
91 Holder
93 Holder
95 Double-headed arrow
97 Double-headed arrow
99 Eye pupil
101 Digital
103 Entry pupil
105 Aperture stop
107 Optical fiber
109 Collimator optical unit
111 Scanning mirror
113 Beam widening optical unit
115 Deflection mirror
117 MEMS oscillator
RA Axis of rotation

The invention claimed is:

1. An operating microscope for observing an eye comprising:
   a main objective with a focal length between 90 mm and 160 mm; and
   a fundus imaging system positionable in a beam path between the eye and the main objective, the fundus imaging system comprising an ophthalmoscopy magnifier and an optics group,
   wherein the ophthalmoscopy magnifier is configured to image a fundus of an eye into an intermediate image plane,
   wherein the ophthalmoscopy magnifier and the optics group are configured to rotate in and out of the beam path about a similar axis,
   wherein a distance between the optics group and the main objective is at least 2.5 times a distance between the optics group and the intermediate image plane, and
   wherein the ophthalmoscopy magnifier and the optics group are fastened to a shaft that is displaceable parallel to an optical axis of the operating microscope such that displacement of the shaft displaces the ophthalmoscopy magnifier and the optics group a same amount.

2. The operating microscope of claim 1, wherein the optics group includes first dispersion properties that match second dispersion properties of the ophthalmoscopy magnifier so that the optics group compensates a chromatic aberration of the ophthalmoscopy magnifier.

3. The operating microscope of claim 2,
   wherein the ophthalmoscopy magnifier is configured to form an intermediate image in the intermediate image plane situated between the ophthalmoscopy magnifier and the main objective, and
   wherein the optics group is arranged between the intermediate image plane and the main objective.

4. The operating microscope of claim 1, wherein the distance of the optics group from the main objective is 2.5 times the distance of the optics group from the intermediate image plane.

5. The operating microscope of claim 1, wherein the main objective is a varioscope objective, wherein the focal length is configured to vary between 90 mm and 160 mm.

6. The operating microscope of claim 5, wherein the fundus imaging system comprises at least two interchangeable ophthalmoscopy magnifiers.

7. The operating microscope of claim 1, further comprising at least one digital image sensor for recording an image.

8. The operating microscope of claim 7, further comprising at least one software module or hardware module for digital magnification of the image recorded by the image sensor.

9. The operating microscope of claim 1, further comprising an optical coherence tomography (OCT) section configured to maintain a distance between the eye and the optics group.

10. The operating microscope of claim 9, wherein the fundus imaging system comprises a distance adjustment system configured to adjust a distance between the ophthalmoscopy magnifier and the eye.

11. The operating microscope of claim 10, wherein the distance adjustment system comprises:
   a motor for a motor-controlled adjustment of the distance between the ophthalmoscopy magnifier and the eye, and
   a control unit connected to the OCT section and the motor, wherein the control unit is configured to (1) determine a distance between the operating microscope and a fundus of the eye based on an OCT signal obtained by the OCT section and (2) adjust the distance between the ophthalmoscopy magnifier and the eye based on the determined distance between the operating microscope and the fundus of the eye.

12. An operating microscope for observing an eye comprising:
   a main objective with a focal length between 100 mm and 135 mm; and
   a fundus imaging system positionable in the beam path between the eye and the main objective, the fundus imaging system comprising an ophthalmoscopy magnifier and an optics group,
   wherein the ophthalmoscopy magnifier is configured to image a fundus of an eye into an intermediate image plane,
   wherein the ophthalmoscopy magnifier is formed from a single glass material having first dispersion properties causing a transverse chromatic aberration,
   wherein the optics group is configured to have second dispersion properties that match the first dispersion properties of the ophthalmoscopy magnifier so as to compensate the transverse chromatic aberration caused by the first dispersion properties of the ophthalmoscopy magnifier,
   wherein the optics group is positioned between the intermediate image plane and the main objective, and the optics group is closer to the intermediate image plane than the main objective, and
   wherein the ophthalmoscopy magnifier and the optics group are fastened to a shaft that is displaceable parallel to an optical axis of the operating microscope such that displacement of the shaft displaces the ophthalmoscopy magnifier and the optics group a same amount.

* * * * *